(12) United States Patent
Fercik Grant et al.

(10) Patent No.: US 9,763,667 B2
(45) Date of Patent: Sep. 19, 2017

(54) EMBOLIZATION COIL WITH BARBED FIBER

(71) Applicant: Cook Medical Technologies LLC, Bloomington, IN (US)

(72) Inventors: Carrie L. Fercik Grant, Ellettsville, IN (US); Kurt J. Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/205,666

(22) Filed: Mar. 12, 2014

(65) Prior Publication Data

US 2014/0277090 A1 Sep. 18, 2014

Related U.S. Application Data

(60) Provisional application No. 61/781,921, filed on Mar. 14, 2013.

(51) Int. Cl.
*A61M 29/00* (2006.01)
*A61B 17/12* (2006.01)
*A61B 17/06* (2006.01)

(52) U.S. Cl.
CPC .... *A61B 17/12145* (2013.01); *A61B 17/1215* (2013.01); *A61B 17/12031* (2013.01); *A61B 17/12109* (2013.01); *A61B 17/12113* (2013.01); *A61B 2017/06176* (2013.01)

(58) Field of Classification Search
CPC ............... A61F 2/013; A61B 17/12145; A61B 17/1215; A61B 17/12109; A61B 17/12113; A61B 17/12031; A61B 2017/06176

USPC ......................................................... 606/200
See application file for complete search history.

(56) References Cited

U.S. PATENT DOCUMENTS

| 3,423,284 | A | * | 1/1969 | Gneisz Josef | ........... D06Q 1/02 162/146 |
| 5,382,260 | A | | 1/1995 | Dormandy, Jr. et al. | |
| 5,476,472 | A | | 12/1995 | Dormandy, Jr. et al. | |
| 5,658,308 | A | | 8/1997 | Snyder | |
| 6,024,754 | A | | 2/2000 | Engelson | |
| 6,143,007 | A | * | 11/2000 | Mariant | ............. A61B 17/1215 606/151 |
| 7,896,899 | B2 | | 3/2011 | Patterson et al. | |
| 8,267,961 | B2 | | 9/2012 | Popadiuk et al. | |
| 2004/0153120 | A1 | * | 8/2004 | Seifert | ............. A61B 17/00491 606/200 |

(Continued)

FOREIGN PATENT DOCUMENTS

| DE | 10 2007 025 466 A1 | 12/2008 |
| WO | 2008/106171 A1 | 9/2008 |

*Primary Examiner* — Richard Louis
(74) *Attorney, Agent, or Firm* — Brinks Gilson & Lione

(57) ABSTRACT

A system for occluding a blood vessel includes an embolization coil having barbed fibers coupled thereto. The coil can be delivered in a straight configuration and then transition into a larger coiled structure. The barbed fibers can overlap within a lumen defined by the larger coiled structure and attached to each other to define a mesh. The barbs of the barbed fiber can limit the fibers from being pulled out of the coil, as well as provide anchoring of the coil to the blood vessel in which the coil is deployed. The barbed fibers can also be used to anchor two coils to each other.

18 Claims, 5 Drawing Sheets

(56) References Cited

U.S. PATENT DOCUMENTS

| | | |
|---|---|---|
| 2005/0004598 A1* | 1/2005 | White et al. .................. 606/200 |
| 2005/0228436 A1* | 10/2005 | Lorenzo et al. .............. 606/200 |
| 2006/0036281 A1* | 2/2006 | Patterson et al. ............. 606/200 |
| 2006/0116711 A1* | 6/2006 | Elliott .............. A61B 17/12022 |
| | | 606/200 |
| 2006/0212127 A1* | 9/2006 | Karabey et al. ........... 623/23.75 |
| 2007/0083226 A1* | 4/2007 | Buiser et al. ................. 606/200 |
| 2007/0083266 A1* | 4/2007 | Lang ................... A61F 2/30756 |
| | | 623/17.11 |
| 2007/0239194 A1* | 10/2007 | Tran et al. .................... 606/191 |
| 2007/0250051 A1* | 10/2007 | Gaston .................. A61B 18/18 |
| | | 606/33 |
| 2008/0221554 A1* | 9/2008 | O'Connor ........ A61B 17/12022 |
| | | 604/526 |
| 2010/0010533 A1 | 1/2010 | Burke et al. |
| 2012/0143349 A1* | 6/2012 | Peterson .......... A61B 17/06166 |
| | | 623/23.72 |
| 2012/0226304 A1* | 9/2012 | Ryan ................ A61B 17/12031 |
| | | 606/200 |
| 2012/0245629 A1 | 9/2012 | Gross et al. |

\* cited by examiner

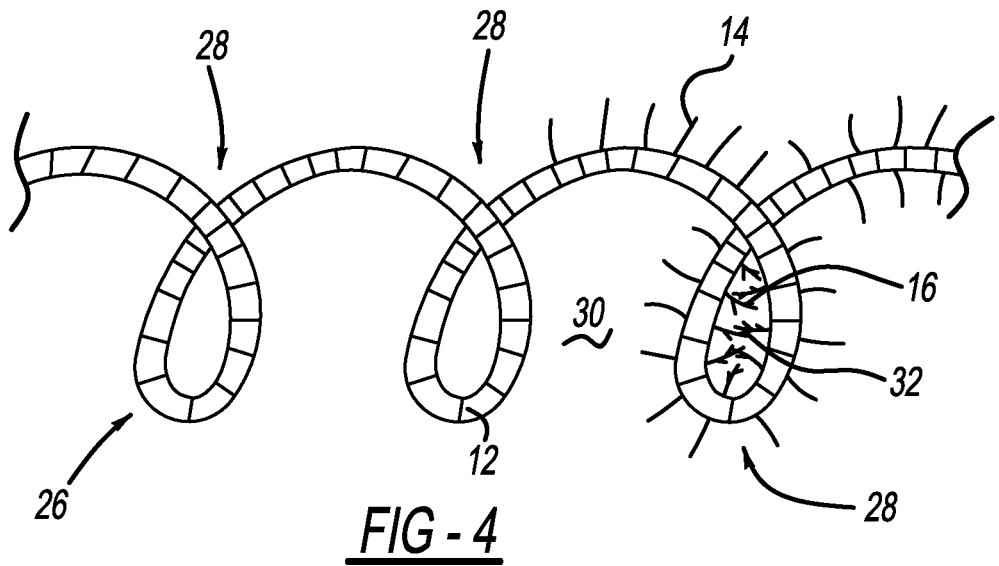
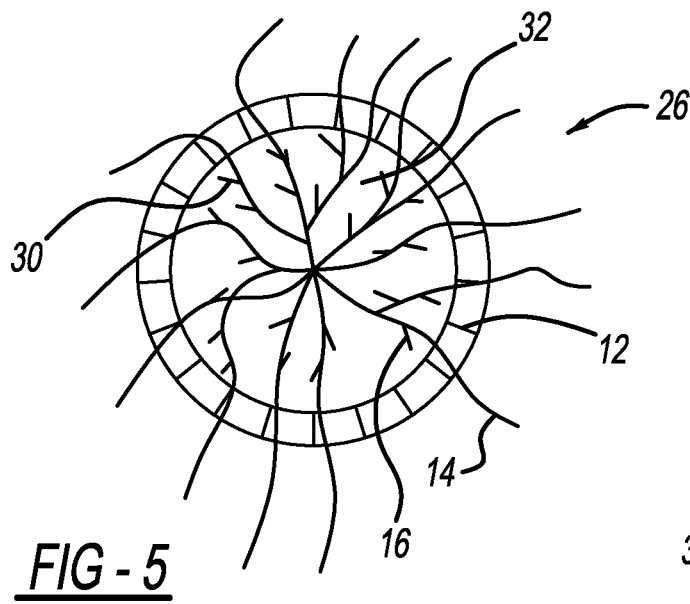
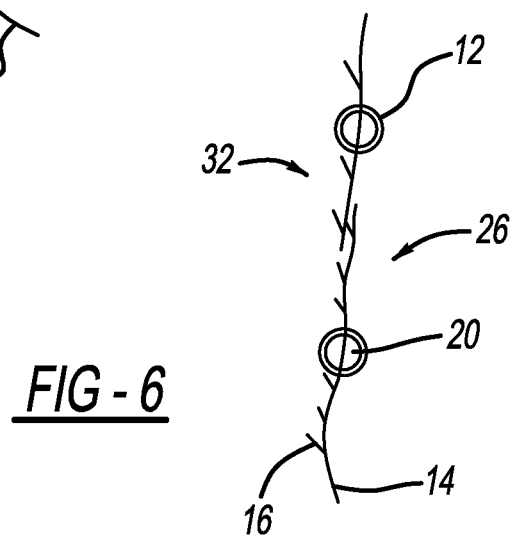

EMBOLIZATION COIL WITH BARBED FIBER

CROSS-REFERENCE TO RELATED APPLICATIONS

This application claims the benefit under 35 U.S.C. §119 (e) of U.S. Provisional Application No. 61/781,921, filed Mar. 14, 2013, which is hereby incorporated by reference in its entirety.

BACKGROUND

The present invention relates to medical devices. More particularly, the invention relates to an occlusion device for occluding fluid flow through a body vessel.

Occlusion devices are well known in the art, and have been used for treatment of various arteriovenous malformations and vericoceles, as well as for various other arteriovenous abnormalities in the body. Occluding devices are also used to repair abnormal shunts between arteries and veins, prevent and reduce blood flow to tumors, stop hemorrhaging as a result of trauma, and stabilize aneurysms to prevent rupture.

One type of occluding device is in the form of an embolization coil. Embolization coils can be formed by a coiled wire that is wrapped in a helical manner to create an elongated coil. The coils can also include fibers that are held between the coils along the length of the coil. The fibers are used to occlude the blood vessel in addition to the material of the coil, as the coil on its own can still result in a lumen through which blood when flow when the coil is deployed.

SUMMARY

A system for occluding a blood vessel is provided, the system comprising: a first coil having an elongate shape and defining a plurality of loops and a lumen, wherein the coil has a first configuration that is generally straight; a plurality of fibers coupled to the first coil and extending outwardly therefrom; and a plurality of barbs coupled to the plurality of fibers, wherein the barbs limit the fibers from being pulled out of the coil.

In another form, a method for occluding a blood vessel is provided, the method comprising: delivering a coil into a blood vessel, wherein the coil includes a plurality of barbed fibers coupled thereto; contacting a wall of the blood vessel with the barbed fibers; anchoring the barbed fibers to the blood vessel wall; and occluding the blood vessel with the coil and the barbed fibers.

BRIEF DESCRIPTION OF THE DRAWINGS

FIG. 4 is a schematic view of the coil being shaped into a larger coil;

FIG. 5 is a side view of the coil in the form of the larger coil;

FIG. 6 is a cross-sectional view of the coil in the form of the larger coil;

DETAILED DESCRIPTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
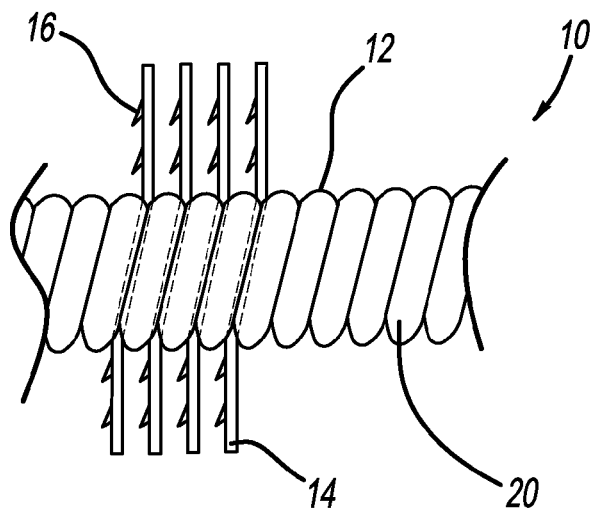
FIG. 1 is a partial front view of an occlusion device having a coil and barbed fibers.
Figure 2:
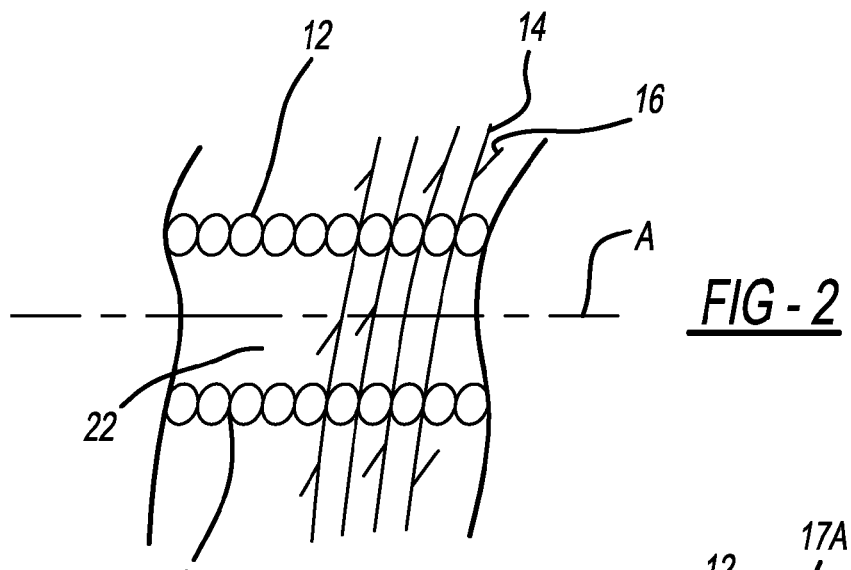
FIG. 2 is a cross-sectional view of the coil.
Figure 3:
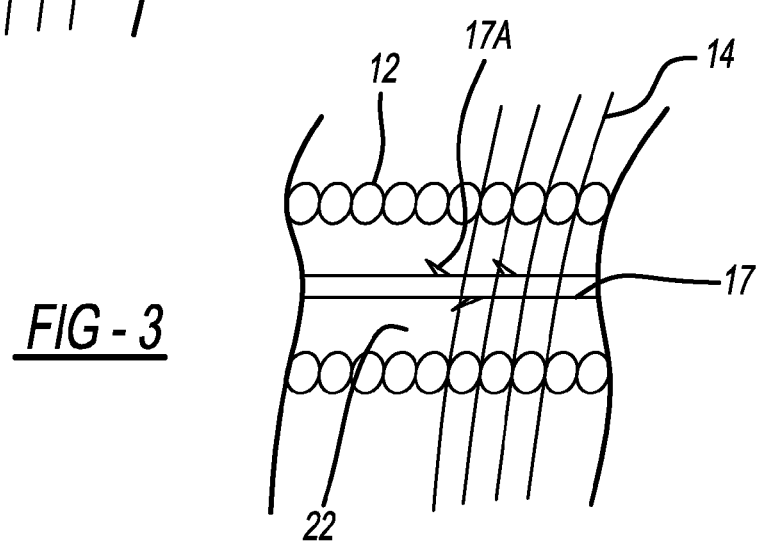
FIG. 3 is a cross-sectional view of another embodiment of the coil.

Referring now to the drawings, FIGS. 1-14 illustrate an occlusion device 10 in the form of a coil 12 having fibers 14 held in place by the coil 12. In one form, as shown in FIGS. 1 and 2, the fibers 14 can include barbs 16 that keep the fibers 14 in place and act to anchor the coil 12 within the body vessel in which the coil 12 is inserted. In another form, the fibers 14 can be smooth and without barbs, and a barbed support member 17 can extend along the coil 12 to grasp the fibers 14 and keep them in place (FIG. 3).

With reference to FIG. 1, the coil 12 can be formed by a wire that is bent or wrapped in a spiral/helical manner to form a plurality of loops 20. The loops 20 can be tightly arranged adjacent each other to define a lumen 22 extending along the length of the coil 12. The coil 12 and lumen 22 extending therethrough thereby defines a longitudinal axis A. The wire that forms the coil 12 can be made from any suitable material known in the art. In one form, the coil 12 can be made from platinum for its radiopacity. One example of coil construction and use can be found in U.S. patent application Ser. No. 10/884,728, filed Jul. 2, 2004, which is hereby incorporated by reference in its entirety. As will be further described below, the coil 12 can be further formed or shaped into other larger shapes, such as a larger coil or a spiral, or the coil 12 can be made flexible enough to bend and fold to conform the shape of the cavity in which it is inserted.

As shown in FIG. 2, the loops 20 that form the coil 12 also define interfaces 24 between adjacent loops 20. Due to the spiral shape of the wire forming the coil 12, it will be appreciated that the interfaces 24 are continuous with each other as they spiral around the coil 12. Thus, the reference to the interfaces 24 refers to different interface locations between adjacent portions of the coil 12 that define the loops 20.

Preferably, the coil 12 comprises platinum or any other suitable metal, composition, or alloy having between about 50,000 and 350,000 pounds per square inch tensile strength. It has been determined that the tensile strength range described above provides the coil 12 with the capability of being flexible, malleable, and folded.

The coil 12 may be made by any apparatus known in the art. For example, the coil 12 may be made by any commercial coil winding machine such as a roller deflecting apparatus, a mandrel apparatus, or any other suitable means.

In this embodiment, the wire forming the coil 12 may have a length of between about 3 to 20 centimeters. The coil 12, when formed into the coil-shape that defines the lumen 22 therethrough, may have an outer diameter ranging between about 3 and 45 millimeters. For most applications, the outer diameter will not exceed about 25 millimeters. The wire forming the coil 12 may have an outer diameter of between about 0.010 and 0.04 inch. The catheter inner diameter through which the occlusion device may be advanced ranges between about 0.014 and 0.045 inch, depending on the outer diameter of the wire forming the coil 12.

The fibers 14 are arranged transverse to the axis A and extend across the lumen 22 defined by the coil. The fibers 14 are held in place within the interfaces 24 between the loops 20 by friction. The fibers 14 that extend across the lumen 22 also extend outwardly from the coil 12 on both sides so that they are both exposed from the coil 12 and housed within the coil 12. The fibers 12 can extend from the coil 12 at various distances, as desired, to increase the ability of the fibers 14 to occlude a body vessel when the coil 12 is delivered.

With reference to FIG. 2, as described above, the fibers 14 can include barbs 16. The barbs 16 can be disposed at various locations along the length of each fiber 14. For example, the barbs 16 can be arranged so that they are positioned outside of the coil 12 on both sides. Alternatively, the barbs 16 can positioned within the lumen 22 of the coil 12. In another approach, the barbs 16 can be positioned both inside and outside of the coil 12. The various barb arrangements can be used for each of the fibers 14, or for individual fibers 14. For example, some fibers 14 can have barbs 16 on the outside of the coil 12, with others having barbs 16 on the inside of the coil 12, or some fibers 14 could have a combination of both arrangements. It will be appreciated that various arrangements of the barbs 16 on the fibers 14 can be used depending on the needs of the user.

As described above, the fibers 14 are held in place at the interfaces 24 through friction created by adjacent loops 20 of the coil 12. Essentially, the loops 20 squeeze the fibers 14 at the interfaces 24 to hold the fibers 14 in place. However, upon sufficient pulling force on the fibers 14, or bending of the coil 12 to open the interfaces 24 reducing the friction, the fibers 14 can be pulled out of attachment with the coil 12. The barbs 16, being positioned on the fibers 14 at locations outside and/or inside the coil 12, can limit the movement of the fibers 14 and limit the fibers 14 from being removed from the coil 12. In the event a fiber 14 is pulled across the coil 12, the barbs 16 will provide a mechanical stop to the fiber 14, thereby limiting the distance that the fiber 14 will migrate.

The above description related to the fibers 14 being held in place between the loops 20 of the coil 12 refer to the coil 12 in a straight configuration. However, and with reference to FIGS. 4-6, as known in the art, the coil 12 can be subsequently formed to create a larger coil 26 having a plurality of spaced loops 28 that define a secondary lumen 30. The larger coil 26 can have a diameter that generally corresponds to the width of the target occlusion site. Of course, the coil diameter can also be smaller than the target occlusion site. A diameter that is smaller than the target occlusion site may be preferable to a larger or corresponding diameter, because of the lumen 30 that is defined by the coil 26. A larger lumen can result in blood flowing through the lumen 30 rather than blood being occluded.

While a larger diameter lumen 30 can allow blood to flow through the lumen 30 rather than be occluded, the fibers 14 with barbs 16 can operate to block the lumen 30, even for larger diameter coils 26. When the coil 12 is formed into coil 26, the fibers 14 that extend across the lumen 22 of coil 12 will end up extending outwardly from the coil 26 toward the body vessel wall, as well extending inwardly into the lumen 30. Because the fibers extend radially inward into the lumen 30, the fibers 14 can overlap each other within the lumen 30. The overlapping nature of the fibers 14, combined with the barbs 16 disposed thereon, can cause the fibers 14 to become interwoven and tangled due to the barbs 16. Thus, the overlapping fibers 14 with barbs 16 can combine to define a mesh 32 that extends across the lumen 30. This mesh 32 will generally not be created by fibers that are smooth and free of barbs. In the case of barbless fibers, blood can flow past the fibers and cause the fibers to bend in response, thereby reducing the occluding ability of the barbless fibers. The mesh 32, being comprised of interlocked fibers 14 having barbs 16, can be restricted from bending in response to blood flow against them, and can result in increased occluding abilities.

With reference again to FIG. 3, in another form, as described above, the fibers 14 can be free from integrated barbs. In this form, the fibers 14 can extend across the coil 12 and be held in place, in part, by friction at the interfaces 24 between adjacent loops 20. Additional support for the fibers 14 can be provided by the support member 17 can have an elongate shape and include barbs 17a extending outwardly therefrom. The support member 17 can include multiple barbs 17a along its length, extending from various points about its cross-sectional circumference. The barbs 17a disposed along the length of the support member 17 can thereby be configured to grasp or catch the fibers 14 within the lumen 22 of the coil 12. Of course, the support member 17 could also be used with the fibers 14 having barbs 16.

In one form, the barbs 17a can extend at an oblique angle from the support member 17 in the distal direction. Thus, advancing the support member 17 in a proximal direction through the coil lumen 22 will allow the barbs 17a to translate past the fibers 14 extending across the coil lumen 22. The support member 17 can then be refracted slightly in the distal direction, allowing the barbs 17a to catch and grasp the fibers 14. In another form, the barbs 17a can extend at an oblique angle in the proximal direction, the support member 17 can be inserted into the coil lumen 22 in a distal direction.

With the support member 17 extending through the lumen 22 of the coil 12, the fibers 14 are thereby limited from being pulled away or coming loose from their connection to the coil 12. The support member 17 will generally retain the fibers 14 thereto due to the barbs 17a.

As described above, and with reference to FIG. 7, the coil 12 can be formed into larger coil 26, with the fibers 14 extending radially inward and outward from the coil 26. As described above, smooth fibers without barbs can be caused to bend in response to blood flow that can limit occlusion. To counteract this, a plurality of barbed support members 17, previously described, can be inserted into the lumen 30 to grasp and catch the fibers 14 that are without barbs and create the mesh 32 (see FIG. 7). The support member 17 can thereby operate to keep the fibers 14 from bending in response to blood flow, and the occluding ability of the fibers 14 without barbs can be increased. Of course, the support members 17 could still be used with fibers 14 having barbs 16.

Figure 8:
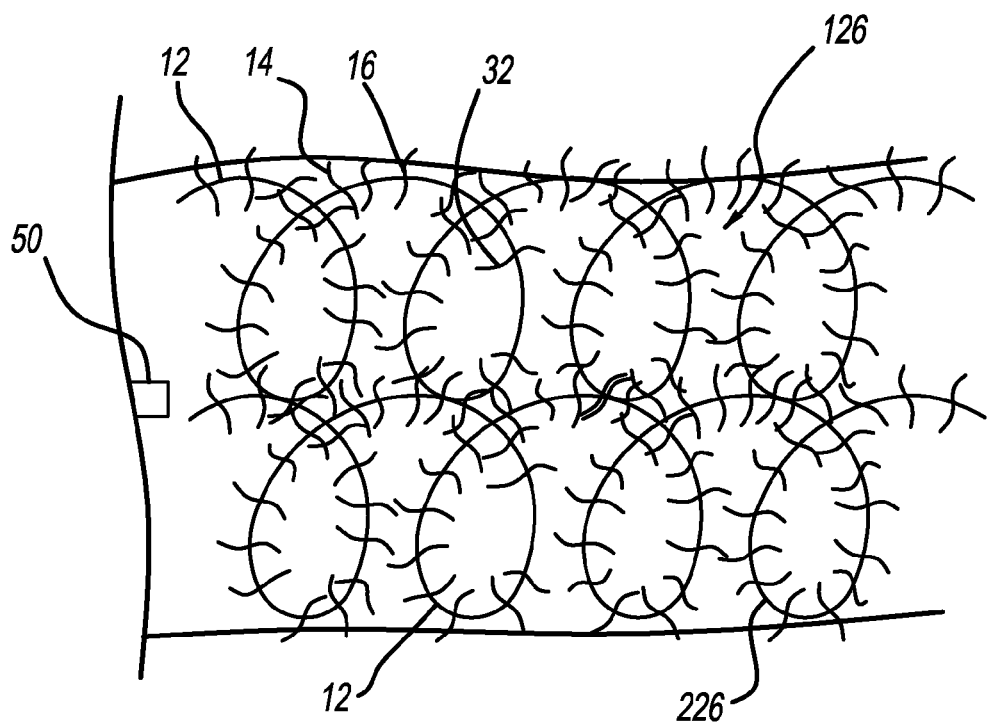
FIG. 8 is a schematic view of the coil delivered within a body vessel along with a second coil.

With reference to FIG. 8, in addition to the barbs 16 limiting the fibers 14 from coming loose from the coil 12, the barbs 16 are also useful for preventing coil migration. Coil migration is an instance where the embolization coil 12, after being delivered to the target location for occluding the blood vessel and embolizing at that location, can move away from the target location. Instances of coil migration should be limited in order to increase the effectiveness of the embolization process. A migrated coil could result in a lack of embolization in the desired area and/or embolizing an undesired area.

The fibers 14 having barbs 16 can be used to anchor the coil 12 at the desired location. In one form, the barbs 16 can be disposed outside of the coil 12, as described above, and can thereby contact the tissue of the body vessel in which the coil is disposed. The barbs 16 will pierce the tissue, causing the coil 12 to remain generally in place. The engagement between the barbs 16 and the tissue will thereby limit coil migration relative to fibers that are free of barbs. The degree to which the fibers 14 attach to the wall due to the barbs 16 can depend on the amount of surface area that is contacted. For example, the greater the contact between the coil 12 and the wall, the greater the surface area that is contacted, thereby increasing the number of barbs 16 that contact the wall and increasing the anchoring ability of the coil 12 with the barbed fibers 14. Similarly, increasing the length of the fiber 14 that is exposed on the outside of the coil and/or increasing the number of barbs 16 that are disposed on the fibers 14 will increase the amount of attached surface are and thereby increasing the anchoring ability of the coil 12 with the barbed fibers 14.

In another form, fibers 14 and barbs 16 of a first coil 126 can become interlocked and/or tangled with fibers 14 and barbs 16 of a second coil 226. As previously described, the coil 12 can be formed into the larger coil 26, which can have a diameter that corresponds to the body vessel or is smaller than the body vessel.

In one form, the first coil 126 and second coil 226 are formed from the coil 12 to have diameters that are smaller than the target vessel. The coils 126 and 226 can each be inserted to the same target vessel adjacent each other. The barbed fibers 14 that extend from the coils 126 and 226 can become interlocked with each other, similar to how the web 32 is created by overlapping fibers 14 within the lumen 30 of the coil 26. The coils 126 and 226 can be placed side by side within the body vessel across the width of the body vessel, or the coils 126 and 226 can be placed longitudinally adjacent each other. In either case, the attachment between the fibers 14 of the first coil 126 and the fibers 14 of the second coil 226 can limit migration of the first coil 126 relative to the second coil 226, and vice versa. Moreover, by attaching the coils 126 and 226 to each other, the overall surface area of the combination increases the contact with the tissue of the body vessel, thereby increasing the attachment and limiting migration of the coils 126 and 226. Each of the above described aspects of the coil 12 and various fiber and barb arrangements can be applied to both the first coil 126 and second coil 226.

The above description has referred to fibers 14 having barbs 16 for providing various anchoring, catching, and grasping abilities. However, it will be appreciated that other types of fibers 14 could also be used that may not have barbs 16 but provide similar grasping and catching abilities when used with the coil 12. The fibers 14 could include circumferential ridges or scales, or other roughening features that can increase the ability of the fibers 14 to become attached to other, entangled, or otherwise held together in a weave or braid while being limited from pulling free. For example, the fibers 14 could have surface characteristics similar to wool fiber, merino fiber, or cashmere fiber. These types of textile fibers are commonly used for felting. Fibers 14 having ridges, scales, or the like can be used like the barbs 16 to create the mesh 32 or a type of felted structure, and can be attached to each other or entangled to limit migration of the coil 26 to which they are attached. It will be appreciated that the above references to barbs 16 could also apply to ridges, scales, or the like.

Figure 9:
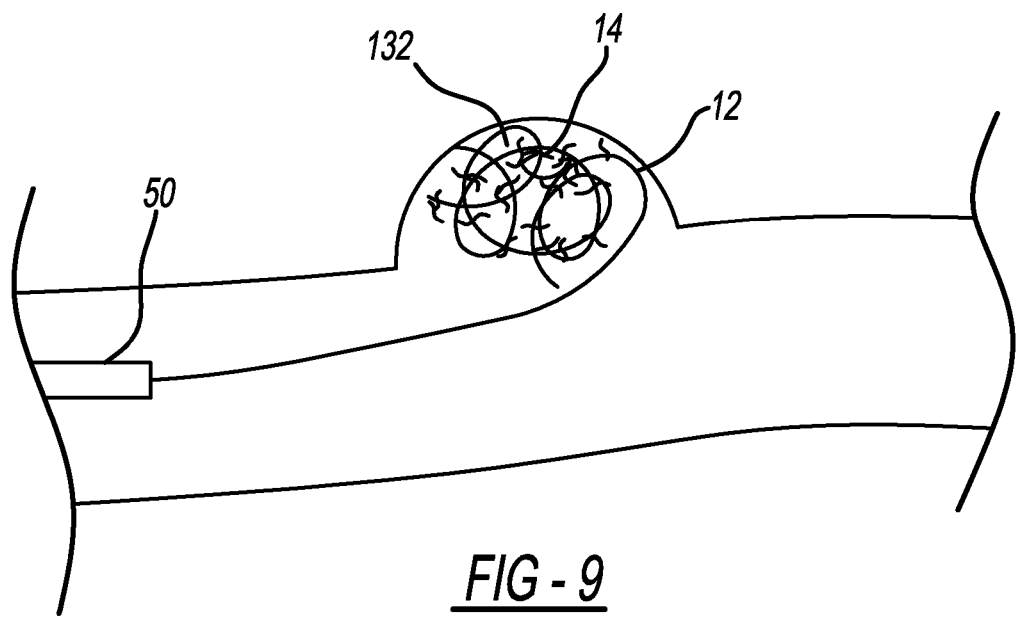
FIG. 9 is a schematic view of the coil delivered within a body vessel and being bent to conform to the shape of the body vessel.

The above description has also referred to the coil 12 being formed into the coil 26 that defines a larger lumen 30 in which the fibers can become attached to each other, creating the mesh 32 and providing increased occlusion abilities. However, the coil 12 can also be made highly flexible such that it is not formed into a secondary shape. Rather, the coil 12 can be flexible enough to fold over itself and generally conform to the size and shape of the body vessel to provide occlusion, as shown in FIG. 9. The folding of the coil 12 within the body vessel can be generally random, and the coil 12 can twist and turn and create a nest like structure. In this form, the fibers 14 having barbs 16 or other structure can attach to themselves to define a mesh 132. Additional coils 12 can be introduced to the area and become attached similar to the side by side coils 126 and 226 described above, with the fibers 14 of adjacent coils 12 becoming intertwined with each other. The various above described coil, fiber, and barb arrangements and alternatives described above can be used in this manner.

Figure 10:
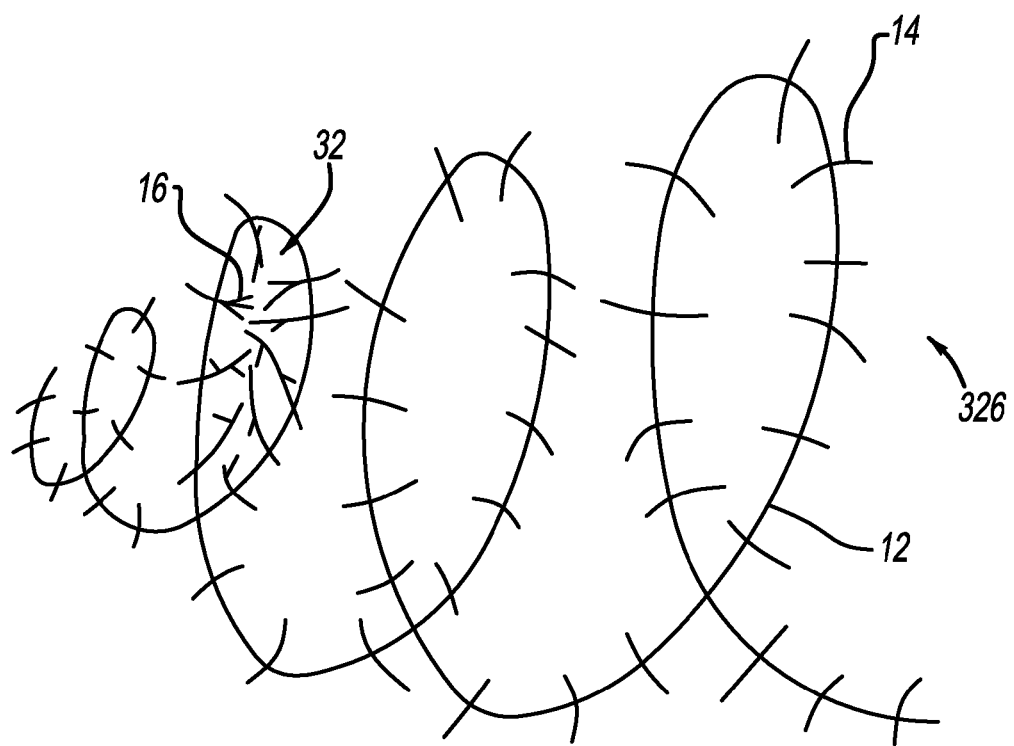
FIG. 10 is a schematic view of the coil being shaped into a conical shaped spiral.
Figure 11:
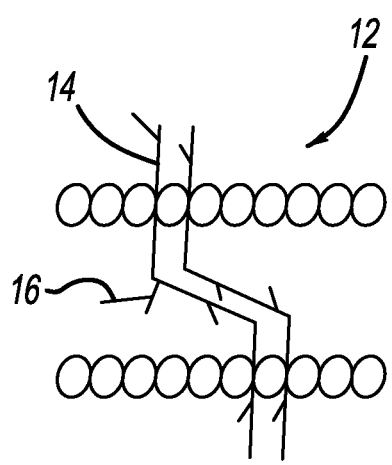
FIG. 11 is a schematic view of the fibers being held by the coil in another embodiment.
Figure 12:
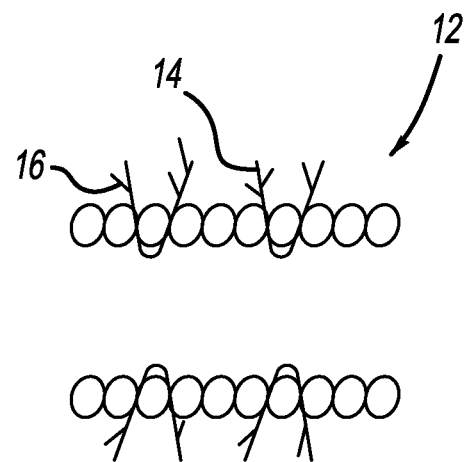
FIG. 12 is a schematic view of the fibers being held by the coil in yet another embodiment.

With reference to FIG. 10, in another form, the coil 12 can be formed into a spiral shaped coil 326. The fibers 14 will similarly form the mesh 32 when they overlap within the spiral shape. If the fibers 14 are each the same length, the mesh 32 can be more dense at the narrow end of the spiral than the wide end of the spiral. In another approach, the fibers 14 can increase in length toward the wide end of the spiral shape to increase the density of the mesh 32 at that end. The various above described coil, fiber, and barb arrangements and alternatives described above can be used in this manner.

Figure 13:
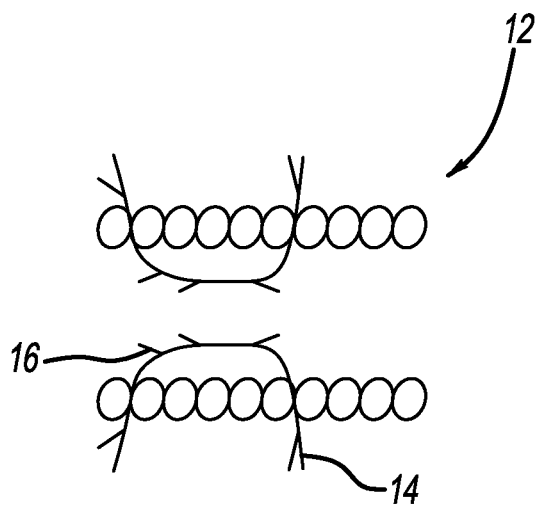
FIG. 13 is a schematic view of the fibers being held by the coil in still another embodiment.

It will be appreciated that other shapes of coils known in the art could also be used with the barbed fibers 14 extending from the coil body. Moreover, the fibers 14 can be attached to the coil 12 in other manners known in the art, such as inserting the fibers 14 into the coil 12 and extending them along the coil 12 before exiting at the other side (FIG. 11), looping or tying the fibers 14 around the loops 20 of the coil 12 (FIG. 12), or weaving the fibers 14 longitudinally along the coil 12 (FIG. 13). It will be appreciated that the advantages of the barbed fibers 14 coupled to the coil 12, or the barbed support member 17 inserted into the coil 12, can be achieved with these other manners of coupling the fibers 14 to the coil 12.

Figure 14:
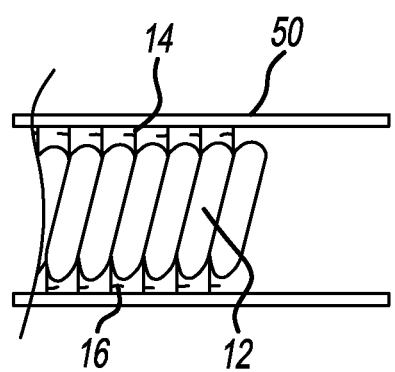
FIG. 14 is a schematic view of the coil within a delivery sheath.

With reference to FIG. 14, to deliver the coil 12 to the desired location within the body, the coil 12 can be housed in a generally straight delivery configuration within a sheath 50, as known in the art. The coil 12 within the sheath 50 can be delivered to the target location through the patient's various tortuous body vessels in a manner known in the art. Upon delivery to the target site, the coil 12 can be extended out from the sheath 50, or the sheath 50 can be retracted, so that the sheath 50 and the coil 12 move relative to each other, thereby exposing the coil 12. In the case where the coil 12 is formed into a predetermined shape, such as the larger coil 26 or the spiral shape 326, or other predetermined shapes, the coil 12 can expand into that shape upon being exposed from the sheath 50.

With reference again to FIG. 8, upon being delivered from the sheath 50, the barbs 16 of the fibers 14 can thereby attach to the wall of the body vessel to anchor the coil 12 within the vessel. Additionally, the fibers 14 can attach to each other via the plurality of barbs 16 and the mesh 32 can be created. The mesh 32 can be created at various locations, including within the lumen 30 of the coil 26 or within the spiral shaped coil 326. The mesh can also be created on the exterior of the coil 26.

Another coil 12 can be introduced toward the body vessel either via a new delivery sheath 50 or through the delivery sheath 50 used for the previously inserted coil 12. The new coil 12 can be exposed in a similar manner, where it can expand into its predetermined shape, or into a random shape corresponding to the shape of the body vessel. The new coil 12 can attach to the previously inserted coil 12 via the barbed fibers 14 of each coil 12. The new coil 12 can thereby be anchored to both the previously inserted coil 12 and the tissue of the body vessel. Similarly, the previously inserted coil 12 can be anchored to the new coil.

Figure 7:
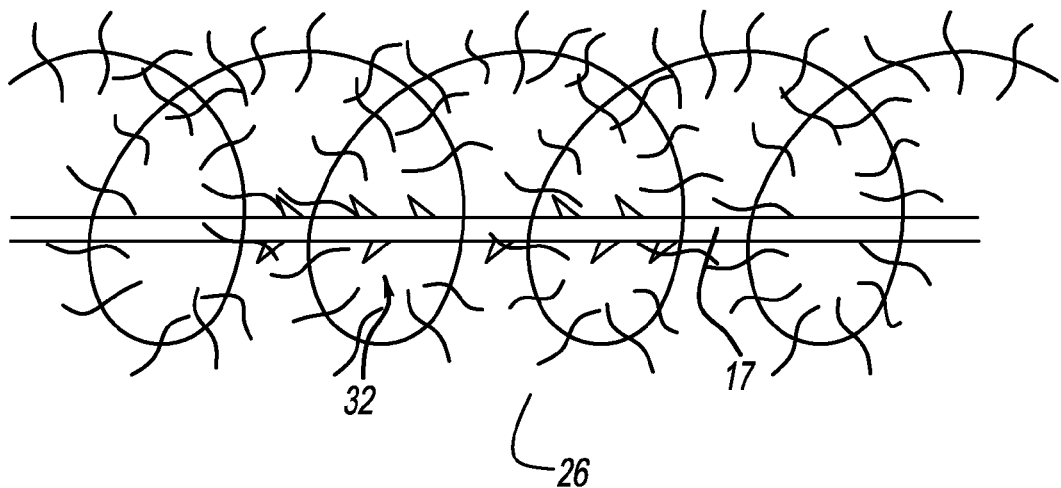
FIG. 7 is another embodiment of the coil being shaped into a larger coil.

Additionally, as shown in FIG. 7, the support member 17 can be inserted through the sheath 50, or another sheath, toward the coils 12 and the fiber 14, if desired. This can be in addition to the use of barbed fibers 14 or for fibers 14 that do not have barbs. Moreover, this can be used in addition to the support member 17 that may have been previously inserted within the lumen 22 of the coil 12 to hold the barbless fibers 14 in place. It will be appreciated that the support member 20 can be inserted to locations where additional attachment among fibers 14 is desired.

With the coil 12 or coils 12 in place within the body vessel and the mesh 32 is created along with the coils 12 being anchored, the coil 12 can thereby occlude the blood vessel and create embolization. Of course, it will be appreciated that not all of the above steps need to be performed to anchor the coils 12 or limit migration while providing embolization.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for occluding a blood vessel, the system comprising:
   a first coil having an elongate shape and defining a plurality of loops and a lumen, wherein the first coil has a first configuration that is generally straight;
   a plurality of fibers coupled to the first coil and extending outwardly therefrom; and
   a plurality of barbs attached to each of the plurality of fibers and extending from each of the plurality of fibers, wherein the barbs limit the fibers from being pulled out of the coil;
   wherein the plurality of loops define a plurality of interfaces between adjacent loops of the plurality of loops, and the plurality of fibers extend through the interfaces and are held in place at the interfaces through friction created by adjacent loops when the first coil is in the first configuration;
   wherein the barbs extending from the plurality of fibers provide a mechanical stop to the fiber against the first coil when the interfaces are expanded and the friction holding the fibers is overcome;
   wherein at least one fiber will migrate across the coil in response to a pulling force that overcomes the friction holding the at least one fiber, and the barbs provide the mechanical stop to limit the distance that the at least one fiber will migrate.

2. The system of claim 1, wherein the first coil has a second configuration wherein the coil is formed into a different shape.

3. The system of claim 1, wherein at least two of the plurality of barbs are disposed on the plurality of fibers outside of the first coil.

4. The system of claim 1, wherein the fibers extend across the lumen of the first coil, and at least one of the plurality of barbs is disposed within the lumen of the first coil.

5. A system for occluding a blood vessel, the system comprising:
   a first coil having an elongate shape and defining a plurality of loops and a lumen, wherein the first coil has a first configuration that is generally straight;
   a plurality of fibers coupled to the first coil and extending outwardly therefrom; and
   a plurality of barbs attached to each of the plurality of fibers and extending from each of the plurality of fibers, wherein the barbs limit the fibers from being pulled out of the first coil;
   wherein the plurality of loops define a plurality of interfaces between adjacent loops of the plurality of loops, and the plurality of fibers extend through the interfaces and are held in place at the interfaces through friction created by adjacent loops when the first coil is in the first configuration;
   wherein the barbs extending from the plurality of fibers provide a mechanical stop to the fiber against the first coil when the interfaces are expanded and the friction holding the fibers is overcome;
   wherein the first coil has a second configuration wherein the coil is formed into a different shape,
   wherein the fibers held by one portion of the first coil longitudinally overlap and contact the fibers held by another portion of the first coil to define a mesh, the fibers being attached to each other via the barbs.

6. The system of claim 5, wherein the second configuration has a helical shape defining a second lumen, and the mesh is disposed within the second lumen.

7. The system of claim 5, wherein the second configuration has a bent shape wherein the coil is folded over itself to create a nest-like structure and the mesh is disposed along the bent shape.

8. The system of claim 5, wherein the second configuration has a conical spiral shape, and the mesh is disposed within the conical spiral shape.

9. A system for occluding a blood vessel, the system comprising:
   a first coil having an elongate shape and defining a plurality of loops and a lumen, wherein the coil has a first configuration that is generally straight;
   a plurality of fibers coupled to the first coil and extending outwardly therefrom; and
   a plurality of barbs coupled to the plurality of fibers, wherein the barbs limit the fibers from being pulled out of the coil; and
   a second coil having barbed fibers coupled thereto, and the first coil is attached to the second coil via an engagement between the barbed fibers of the first coil and the barbed fibers of the second coil.

10. The system of claim 9, wherein the first coil and the second coil are each formed into a larger coil, the first and second larger coils each define second lumens having a longitudinal axis, and the axes of the first and second larger coils are laterally offset.

11. The system of claim 9, wherein the engagement between the barbed fibers of the first and second coils defines a mesh of the barbed fibers.

12. A system for occluding a blood vessel, the system comprising:
   a first coil having an elongate shape and defining a plurality of loops and a lumen, wherein the coil has a first configuration that is generally straight;
   a plurality of fibers coupled to the first coil and extending outwardly therefrom; and
   a plurality of barbs coupled to the plurality of fibers, wherein the barbs limit the fibers from being pulled out of the coil;
   wherein the barbs are disposed on an elongate support member extending through the lumen of the coil, and the elongate support member is coupled to the fibers within the lumen to limit the fibers from being removed from the coil.

13. A method for occluding a blood vessel, the method comprising:
   delivering a coil into a blood vessel, wherein the coil includes a plurality of barbed fibers coupled thereto that limit the fibers from being pulled out of the coil, wherein the coil includes a plurality of loops that define a plurality of interfaces between adjacent loops of the plurality of loops, and the plurality of barbed fibers extend through the interfaces and are held in place at the interfaces through friction created by adjacent loops when the coil is in the first configuration, wherein barbs of the barbed fibers extend from the plurality of fibers and provide a mechanical stop to the barbed fibers against the coil when the interfaces are expanded and the friction holding the barbed fibers is overcome;
   contacting a wall of the blood vessel with the barbed fibers;
   anchoring the barbed fibers to the blood vessel wall; and
   occluding the blood vessel with the coil and the barbed fibers;
   wherein the coil has a first condition and a second condition, the first condition is generally straight, the second condition is in the form of a larger coil, and further comprising the step of converting the coil from the first condition to the second condition;
   wherein the larger coil defines a lumen, the barbed fibers extending radially into the lumen, and further comprising the step of overlapping the barbed fibers and connecting adjacent barbed fibers to define a mesh across the lumen.

14. A method for occluding a blood vessel, the method comprising:
   delivering a coil into a blood vessel, wherein the coil includes a plurality of barbed fibers coupled thereto that limit the fibers from being pulled out of the coil, wherein the coil includes a plurality of loops that define a plurality of interfaces between adjacent loops of the plurality of loops, and the plurality of barbed fibers extend through the interfaces and are held in place at the interfaces through friction created by adjacent loops when the coil is in the first configuration, wherein barbs of the barbed fibers extend from the plurality of fibers and provide a mechanical stop to the barbed fibers against the coil when the interfaces are expanded and the friction holding the barbed fibers is overcome, wherein at least one fiber will migrate across the coil in response to a pulling force that overcomes the friction holding the at least one fiber, and the barbs provide the mechanical stop to limit the distance that the at least one fiber will migrate;
   contacting a wall of the blood vessel with the barbed fibers;
   anchoring the barbed fibers to the blood vessel wall; and
   occluding the blood vessel with the coil and the barbed fibers.

15. The method of claim 14, wherein the coil has a first condition and a second condition, the first condition is generally straight, the second condition is in the form of a larger coil, and further comprising the step of converting the coil from the first condition to the second condition.

16. The method of claim 14, further comprising bending the coil such that the coil folds over itself to create a nest-like structure within the blood vessel and interlocking the barbed fibers into a mesh.

17. The method of claim 15, wherein the larger coil has a conical shape.

18. A method for occluding a blood vessel, the method comprising:
   delivering a coil into a blood vessel, wherein the coil includes a plurality of barbed fibers coupled thereto;
   contacting a wall of the blood vessel with the barbed fibers;
   anchoring the barbed fibers to the blood vessel wall; and
   occluding the blood vessel with the coil and the barbed fibers; and
   delivering a second coil into the blood vessel, wherein the second coil includes barbed fibers coupled thereto, and attaching the coil to the second coil via engagement between the barbed fibers of the second coil and the barbed fibers of the coil.

* * * * *